United States Patent [19]
Ackerman

[11] Patent Number: 5,131,094
[45] Date of Patent: Jul. 21, 1992

[54] VISOR

[76] Inventor: Roger C. Ackerman, 28241 Crown Valley Pkwy, #484, Laguna Niguel, Calif. 92677

[21] Appl. No.: 620,656

[22] Filed: Dec. 3, 1990

[51] Int. Cl.[5] ................................................ A61F 9/00
[52] U.S. Cl. ............................................. 2/12; 2/12; 2/181.8
[58] Field of Search .......... 2/12, 15, 171, 171.4, 2/171.5, 171.6, 171.7, 171.8, 177, 179, 181, 181.2, 181.6, 181.8, 182.1, 182.2, 182.3, 182.5, 183, 195, 197, DIG. 11

[56] References Cited

U.S. PATENT DOCUMENTS

| | | | |
|---|---|---|---|
| 1,170,052 | 2/1916 | Diener | 2/181.8 |
| 1,510,482 | 10/1924 | Kramer | 2/181.8 |
| 2,286,202 | 6/1942 | Fischer | 2/182.1 |
| 4,292,689 | 10/1981 | Townsend | 2/12 |
| 4,481,681 | 11/1984 | Hankin | 2/183 |
| 4,856,116 | 8/1989 | Sullivan | 2/12 |
| 4,945,575 | 8/1990 | Townsend | 2/12 |
| 4,951,320 | 8/1990 | Yoon | 2/181.2 |

Primary Examiner—Werner H. Schroeder
Assistant Examiner—Diana L. Biefeld
Attorney, Agent, or Firm—Hawes & Fischer

[57] ABSTRACT

A lightweight, low cost sun and sports visor that is comfortably fit and reliably attached to a wearer's head. According to a first embodiment, the visor includes a headband, having a series of alternating ridges and valleys that establishes spaces through which air may flow to ventilate the forehead. A pair of side straps are slidably adjustable relative to a respective pair of opposing side bands to releasably attach the visor to the wearer's head. According to a second embodiment, the visor includes a peripherally extending, folded-over headband having an air space or channel running therethrough so that the headband can be compressed into the channel and thereby conform to the shape of and cushion the wearer's forehead to assure a comfortable fit. The channel runs continuously through the headband and each of a pair of opposing side bands so as to receive therein the tops of the ears of the wearer to anchor the visor and prevent sunburn to the ears.

6 Claims, 5 Drawing Sheets

VISOR

BACKGROUND OF THE INVENTION

1. Field of the Invention

This invention relates to a sun and sports visor that is manufactured from a lightweight, relatively soft material to form a comfortable and reliable fit around a wearer's head while ventilating the wearer's forehead with increased air flow.

2. Background Art

Sun and sports visors have long been used by beachgoers, joggers, boaters, ballplayers, etc. as head wear to block bright sunlight, absorb sweat and keep one's hair away from the eyes. However, many of the conventional visors are manufactured with a relatively hard, unyielding material. Consequently, such visors are known to form a tight fit around the head Which can lead to discomfort of the wearer. Such visors are also known to cause headaches if worn for long periods of time. Other conventional visors have no means of ventilating the wearer's head and, as a result, do nothing to cool the wearer's forehead to reduce sweating. Still other conventional visors are known to come loose or slide up and down the wearer's head whenever the wearer experiences bumping or impact forces.

It would therefore be desirable to have available a low cost, lightweight and relatively soft sun and sport visor that could be worn for long periods of time while promoting wearer comfort, a reliable fit, and cooling of the wearer's forehead to reduce excessive sweating.

SUMMARY OF THE INVENTION

In general terms, a lightweight, relatively soft sun and sports visor is disclosed that is manufactured from a minimum number of component parts to reduce cost. According to a first embodiment of the invention, the visor has a headband to be engaged by the wearer's forehead. The headband includes a series of alternating ridges and valleys, such that air spaces are formed between the valleys and the wearer's forehead. Accordingly, air flows through such air spaces to ventilate and cool the wearer's forehead and thereby reduce excessive sweating. The visor also has a pair of opposing, arcuate shaped side bands. Each side band includes a longitudinally extending channel within which a respective side strap is received The side straps are slidably adjustable relative to the channels in the side bands to reliably attach the visor to the wearer's head, regardless of the wearer's hat size.

According to a second embodiment of the invention, the visor includes a peripherally extending headband comprising a flexible strip of material that is folded over to form an inverted, U-shaped channel. The channel defines an air space into which the headband is compressed when engaged by the wearer's forehead. Accordingly, the headband will conform to the shape of the wearer's forehead, whereby to cushion the forehead and assure a comfortable fit. The channel of the headband extends continuously through each of a pair of side bands to receive therein the tops of the wearer's ears. Therefore, the visor is reliably attached to the wearer's head while the wearer's ears will be shielded from sunlight and possible sunburn.

DESCRIPTION OF THE PREFERRED EMBODIMENT

Figure 1:
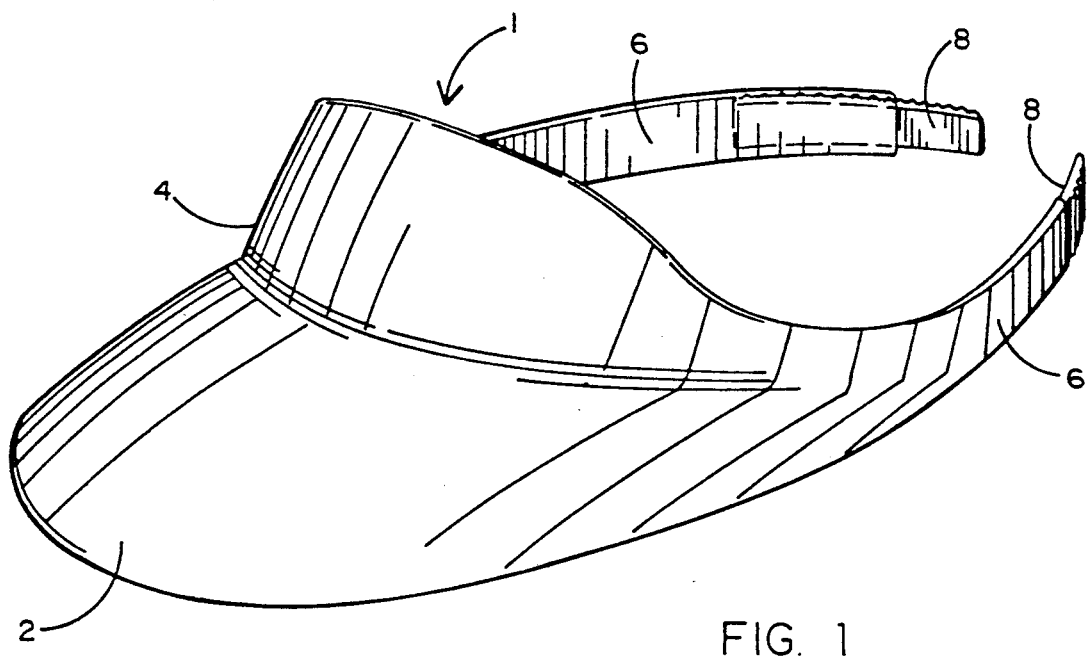
FIG. 1 is a perspective view of a visor according to a first embodiment of the present invention.
Figure 2:
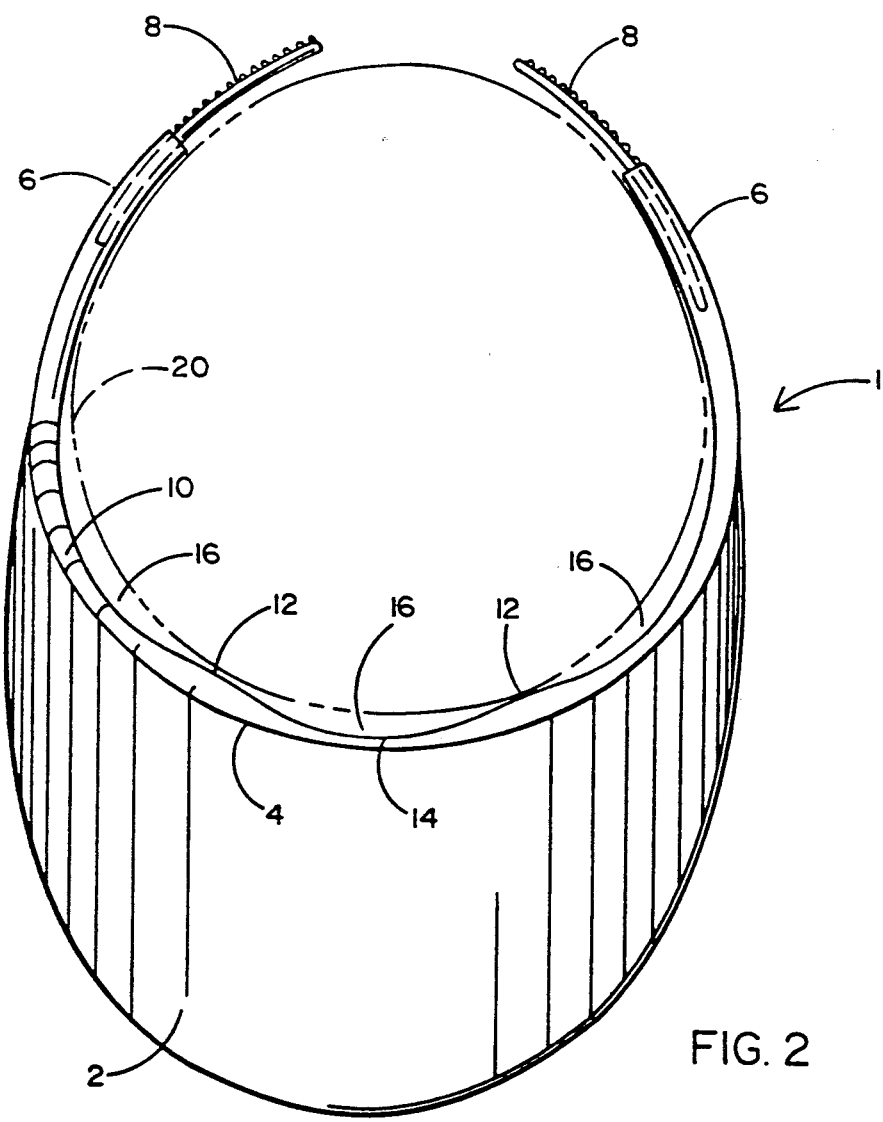
FIG. 2 is a top view of the visor of FIG. 1.
Figure 3:
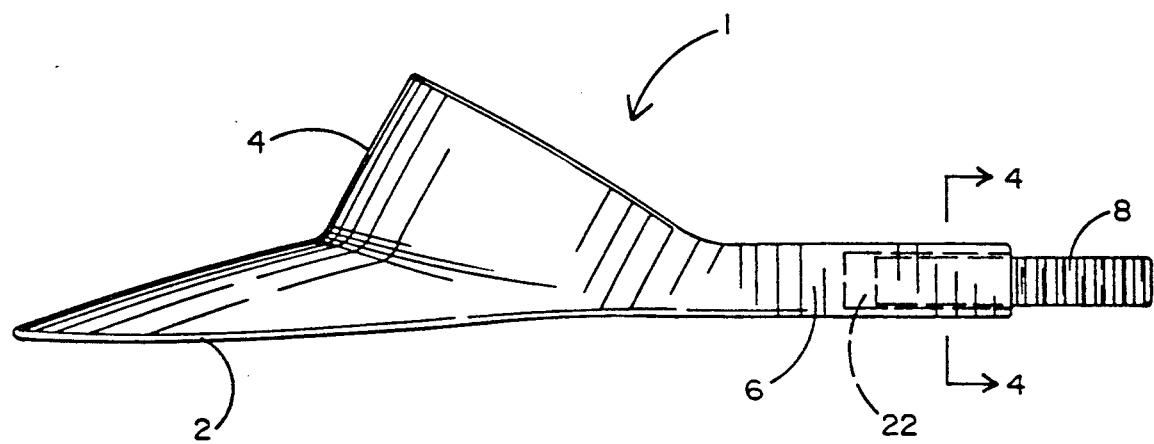
FIG. 3 is a side view of the visor of FIG. 1.
Figure 6:
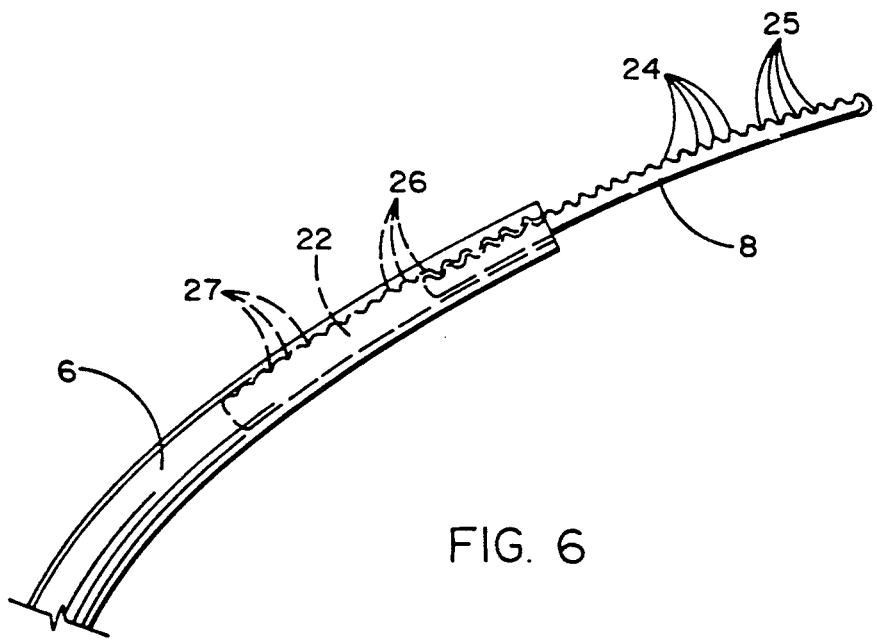
FIGS. 5 and 6 illustrate the slidably adjustable nature of a side strap relative to a respective side band to reliably attach the visor of FIG. 1 to the head of a wearer.
Figure 5:
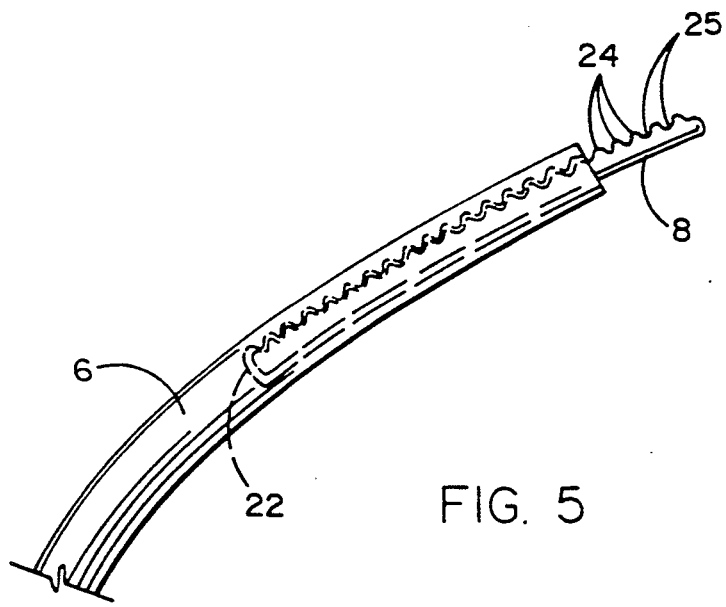

The sun and sports visor 1 which forms a first embodiment of the present invention is described while initially referring to FIGS. 1 and 2 of the drawings. Visor 1 is preferably manufactured (e.g. molded) from a lightweight flexible plastic material, such as polypropylene, polyethylene, or the like, and includes the traditional bill 2, which shields a wearer's eyes from overhead sunlight, and a crown 4 which is coextensively formed with and extended upwardly from bill 2. However, it is to be understood that the soon to be described advantages of this invention are also available to a visor having no crown. Visor 1 also includes a pair of opposing, arcuate-shaped side bands 6 which generally conform to the shape of the wearer's head. As will be described in greater detail hereinafter while referring to FIGS. 3–6, each side band 6 has a respective side strap 8 which is slidably adjustable to enable the visor 1 to be reliably attached to the wearer's head, regardless of hat size.

As is best shown in FIG. 2, a headband 10 extends around the periphery of the crown 4 of visor 1 so as to engage the 3 forehead of the wearer. Headband 10 is preferably a thin piece of plastic, although the headband may optionally be covered with a soft, porous material to absorb sweat at the wearer's forehead In accordance with an important detail of the visor 1, the headband 10 is formed with a series of alternating ridges 12 and valleys 14. Thus, when the visor 1 is worn around the wearer's head (shown by phantom lines at reference numeral 20), the ridges 12 will contact and the valleys 14 will be spaced form the wearer's forehead. Accordingly, one or more air spaces or ventilation gaps 16 are established between each successive pair of ridges 12. That is to say, and unlike conventional visors, the headband 10 is turned forward of the wearer's head 20 at the valleys 14 so as to create spaces 16 through which air may flow to ventilate the wearer's forehead. The number of air spaces 16 shown in the drawings is for the purpose of example only, and headband 10 may be formed to include any suitable number of ridges 12, valleys 14 and air spaces 16.

Another important detail of the present visor 1 is described while referring to FIGS. 3–6 of the drawings. As earlier disclosed, the opposing side bands of visor 1 include respective slidably adjustable side straps 8. More particularly, each side band 6 includes a hollow, longitudinally extending channel 22 formed therein (best shown in FIG. 6). Each side strap 8 is preferably a single piece of relatively flexible plastic having a series of alternating teeth 24 and slots 25 which project from at least one side thereof. Likewise, each channel 22 has a series of alternating slots 26 and teeth 27 formed at the interior thereof. Thus, each side strap 8 is adjustably positioned and retained within its respective channel 22 of side strap 6 by interlocking successive ones of the teeth 24 of side band 8 within corresponding slots 26 of channel 22 and teeth 27 of channel 22 within corresponding slots 25 of side strap 8. The receipt of teeth 24 and 27 within slots 25 and 26 act to frictionally and releasably secure side strap 8 to side band 6 within the hollow channel 22 thereof. Of course, the side straps 8 may be slidably repositioned within channels 22 from a fully retracted position (of FIG. 5) to a fully extended position (of FIG. 6). The precise locations of side strap 8 within channels 22 and relative to the back of the wearer's head depend upon the size of the wearer's head and the degree of tightness desired by the wearer for securing visor 1 to his head.

FIGS. 7-10 of the drawings show a sun and sports visor 30 that is formed in accordance with a second embodiment of the present invention. To minimize production costs, visor 30 is preferably manufactured (e.g. molded) from a single piece of lightweight, flexible plastic material. Like the visor 1 of FIGS. 1-6, the visor 30 includes the traditional outwardly extending bill 32 and an optional, upwardly extending crown 34. Visor 30 also includes a pair of opposing, arcuate-shaped side bands 36 which depend from the crown 34 and generally conform to the shape of the wearer's head.

Figures 4, 10:
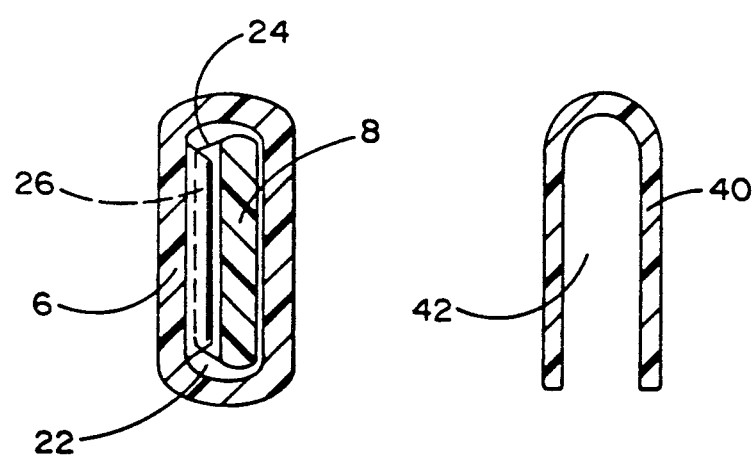
FIG. 4 is a cross-section taken along lines 4—4 of FIG. 3.
FIG. 10 is a cross-section taken along lines 10—10 of FIG. 8.
Figure 7:
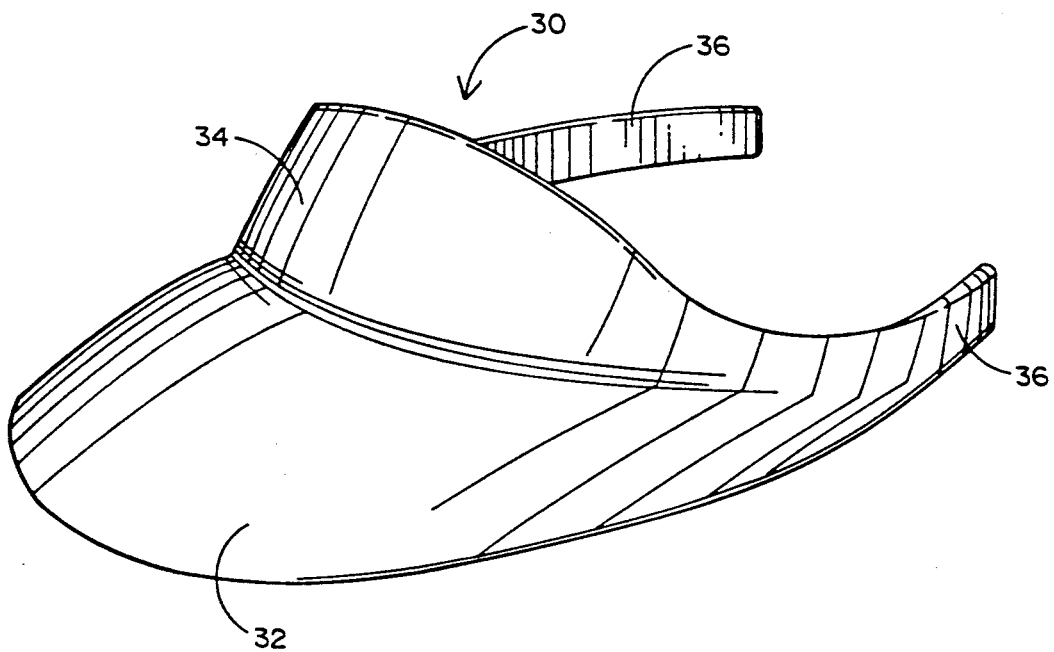
FIG. 7 is a perspective view of a visor according to a second embodiment of the present invention.
Figure 9:
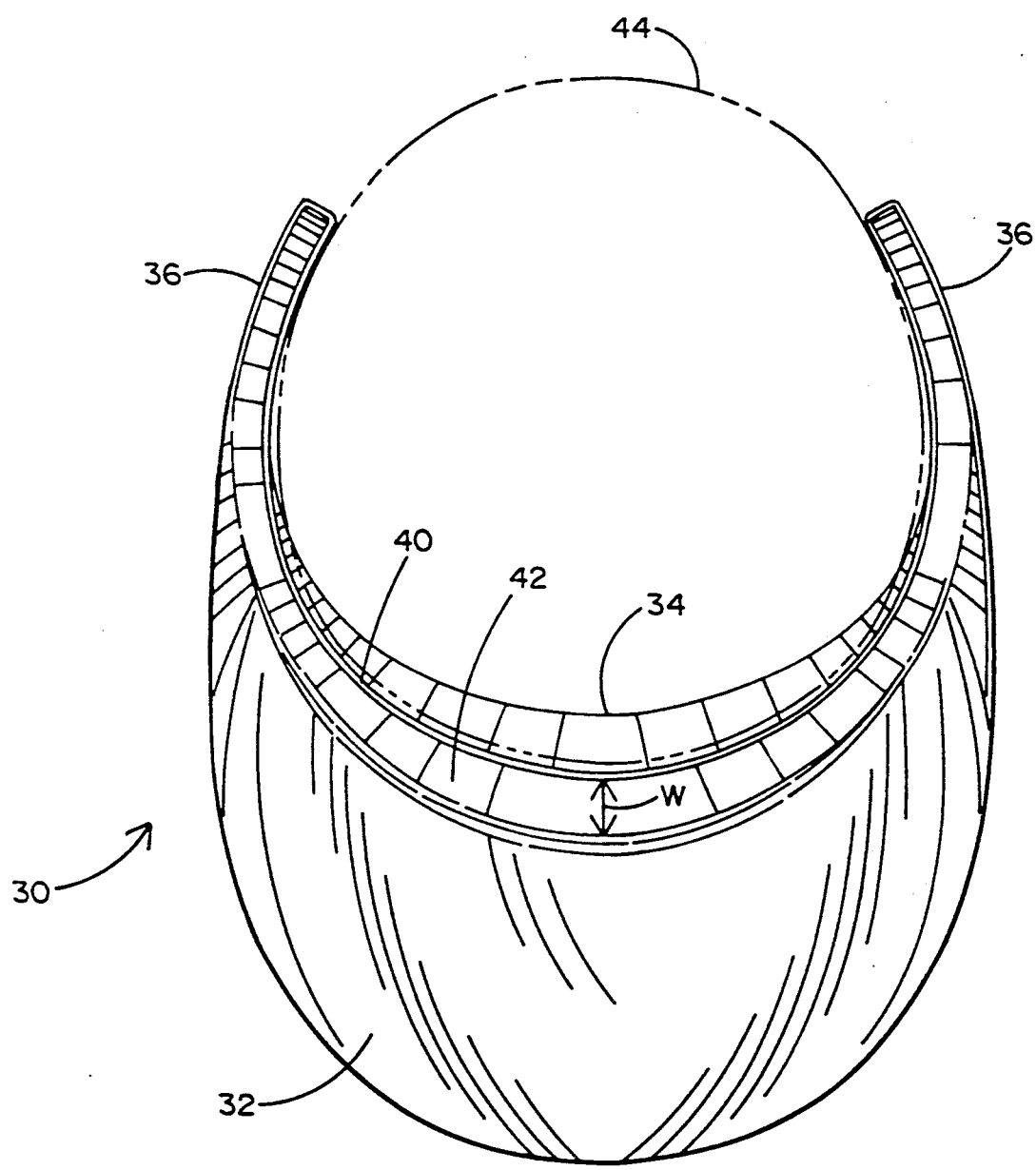
FIG. 9 is a bottom view of the visor of FIG. 7.

Referring now to FIG. 9 of the drawings, the bottom of visor 30 is shown. Visor 30 includes a peripheral headband 40 which is formed by a relatively thin, flexible piece of plastic material that is folded over itself and located behind crown 34 so as to be engaged by the wearer's forehead. As is best shown in FIG. 10, the folded headband 40 comprises an inverted, U-shaped channel 42 that extends completely around the visor so as to extend continuously through headband 40 and side bands 36 for the purpose of providing the wearer with two important advantages. By way of a first advantage, and continuing to refer to FIG. 9, the wearer's head (shown in phantom lines and represented by reference numeral 44) is spaced rearwardly of the bill 32 of visor 30 by an air space corresponding to the width, designated W, (e.g. approximately ⅛") of the channel 42 that is formed between the sides of headband 40. Because of its flexible nature, the headband 40 may be compressed slightly into channel 42 when the visor 30 is worn and the wearer's forehead exerts a pushing force upon said headband 40. By virtue of the air space defined by channel 42, the headband 40 will conform to the shape of and cushion the wearer's forehead. The foregoing results in a much softer and more comfortable fit of visor 30, as opposed to conventional visors which have only a strip of non-yielding hard plastic to engage the wearer's head.

Figure 8:
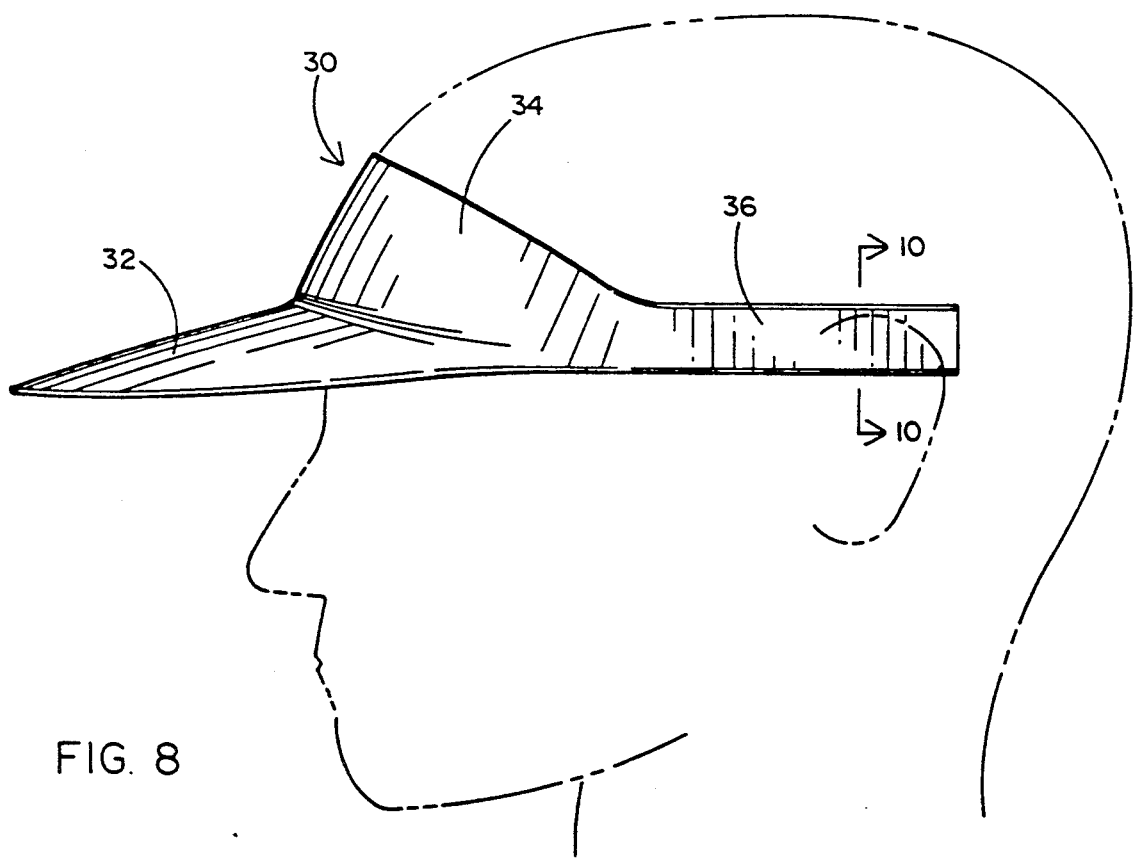
FIG. 8 is a side view of the visor of FIG. 7 fitted to the head of a wearer.

By way of a second advantage of visor 30, and referring concurrently to FIGS. 8 and 9, the length of side bands 36 through which channel 42 extends is elongated to reach the wearer's ears (best shown in FIG. 8). Thus, when the visor 30 is worn, the channel 42 through side bands 36 is positioned to receive the tops of the wearer's ears therein so as to reliably attach visor 30 to the wearer's head and shield the wearer's ears from the rays of the sun.

It will be apparent that while a preferred embodiment of the invention has been shown and described, various modifications and changes may be made without departing from the true spirit and scope of the invention. For example, although the advantages of the present invention have been described with regard to a visor, it is to be understood that such comfort and fit advantages are also applicable to other headwear including, but not limited to, a baseball-type cap, and the like. Having thus set forth a preferred embodiment of the invention, what is claimed is:

1. Headwear comprising a forwardly projecting bill to be positioned in front of a wearer's forehead, a pair of opposing side bands connected to and extending rearwardly of the bill at the sides of the wearer's head, and a headband interconnected with said bill, said headband having a first non-deformable surface which is engaged and supported by the wearer's forehead and a second non-deformable surface communicating with said first surface and spaced forwardly of the wearer's forehead so that a gap of substantially fixed dimension is created between the second non-deformable surface of said headband and the wearer's forehead through which air flows transversely relative to the bill to ventilate the forehead.

2. The headwear recited in claim 1, wherein said first surface of said headband is a ridge which engages the wearer's head and said second surface is a valley connected to said ridge and spaced forwardly of the wearer's forehead so that said gap is established between said valley and the forehead.

3. The headwear recited in claim 1, wherein each of said side bands has a respective sidestrap projecting outwardly therefrom to engage the rear of the wearer's head and thereby attach said headwear to the head.

4. The headwear recited in claim 3, wherein each side band has a longitudinally extending channel formed therein for receiving a respective side strap, said side strap being slidable through said channel for adjusting the position of said side strap relative to the wearer's head.

5. The headwear recited in claim 4, wherein each of said side straps has a plurality of teeth projecting therefrom and each of the channels in said side bands has a plurality of slots, at least some of said teeth being received within corresponding ones of said slots to releasably retain said side straps within respective channels of said side bands.

6. Headwear including a forwardly projecting bill to be positioned in front of a wearer's forehead and comprising:
   side band means extending rearwardly from the bill and having first and second ends lying adjacent opposite sides of the wearer's head;
   a pair of side straps to engage the rear of the wearer's head and thereby attach said headwear to the head;
   a channel formed through each of the first and second ends of said side band means for receiving respective ones of said pair of side straps, such that said side straps are slidable through said channels for adjusting the position of said side straps relative to the wearer's head; and
   at least one tooth projecting from each of said side straps and at least one slot formed in each of said channels, the teeth of said side straps being received within the slots of said channels to releasably retain said side straps within said channels formed in said side band means.

* * * * *